(12) United States Patent
Fleckner et al.

(10) Patent No.: US 9,834,728 B2
(45) Date of Patent: Dec. 5, 2017

(54) PRODUCTION OF FUEL

(71) Applicant: Karen Fleckner, Tacoma, WA (US)

(72) Inventors: Karen Fleckner, Tacoma, WA (US); Michael Kraft Neylon, Tacoma, WA (US)

(73) Assignee: Karen Fleckner, Tacoma, WA (US)

( * ) Notice: Subject to any disclaimer, the term of this patent is extended or adjusted under 35 U.S.C. 154(b) by 0 days.

(21) Appl. No.: 14/900,609

(22) PCT Filed: Jun. 17, 2014

(86) PCT No.: PCT/US2014/042771
§ 371 (c)(1),
(2) Date: Dec. 21, 2015

(87) PCT Pub. No.: WO2014/204981
PCT Pub. Date: Dec. 24, 2014

(65) Prior Publication Data
US 2016/0152899 A1    Jun. 2, 2016

Related U.S. Application Data

(60) Provisional application No. 61/838,103, filed on Jun. 21, 2013.

(51) Int. Cl.
*C10G 2/00* (2006.01)
*C07C 1/04* (2006.01)
*C07C 29/151* (2006.01)
*C07C 41/01* (2006.01)
*C01B 3/32* (2006.01)
*C10K 1/00* (2006.01)
*C01B 3/34* (2006.01)
*C10J 3/82* (2006.01)

(52) U.S. Cl.
CPC .............. *C10G 2/30* (2013.01); *C01B 3/32* (2013.01); *C01B 3/34* (2013.01); *C07C 1/04* (2013.01); *C07C 29/1518* (2013.01); *C07C 41/01* (2013.01); *C10J 3/82* (2013.01); *C10K 1/00* (2013.01); *C01B 2203/025* (2013.01); *C01B 2203/0211* (2013.01); *C01B 2203/0233* (2013.01); *C01B 2203/0244* (2013.01); *C01B 2203/0266* (2013.01); *C01B 2203/062* (2013.01); *C01B 2203/1241* (2013.01); *C10G 2300/1011* (2013.01); *C10J 2300/0946* (2013.01); *C10J 2300/0976* (2013.01); *C10J 2300/1838* (2013.01); *C10J 2300/1853* (2013.01); *Y02E 50/32* (2013.01); *Y02P 20/145* (2015.11); *Y02P 30/20* (2015.11)

(58) Field of Classification Search
CPC .............. C01B 3/32; C01B 2203/0233; C01B 2203/0244; C01B 2203/025; C01B 2203/0266; C07C 29/1518; C07C 41/01; C10G 2/30; C10G 2300/1011; C10K 1/00; Y02E 50/32; Y02P 30/20; Y02P 20/145
See application file for complete search history.

(56) References Cited

U.S. PATENT DOCUMENTS

| | | | |
|---|---|---|---|
| 5,908,963 A | 6/1999 | Voss et al. | |
| 6,774,148 B2 * | 8/2004 | O'Rear | C01B 3/02 252/373 |
| 8,690,975 B2 | 4/2014 | Tsangaris | |
| 2009/0151251 A1 | 6/2009 | Manzer | |
| 2010/0152496 A1 * | 6/2010 | Dumenil | C12P 7/10 568/840 |
| 2011/0036014 A1 | 2/2011 | Tsangaris | |
| 2011/0224462 A1 * | 9/2011 | Ditzel | C07C 29/149 568/885 |

OTHER PUBLICATIONS

"Elemental Analysis of Wood Fuels: Final Report", New York State Energy Research and Development Authority, NYSERDA Report, Jun. 2013, pp. 1-88.*
M.W. W Millke, V. Wong, E.A. McBean, "Describing Variability of MSW Composition Data with the Log-Logistic Distribution", Waste Manag. Res., 26(4), p. 355-61 (2008).*

* cited by examiner

*Primary Examiner* — Medhanit Bahta
(74) *Attorney, Agent, or Firm* — DLA Piper LLP (US)

(57) ABSTRACT

The present invention concerns the production and use of feedstock streams. Specifically, the present invention provides a process for the production of a commodity using two or more feedstock streams. Each feedstock stream is processed into a common intermediate and subsequently processed into a final product, such as electrical energy, a liquid fuel or a liquefied fuel, such as methanol, dimethyl ether, synthetic gasoline, diesel, kerosene, or jet fuel. The common intermediate may be synthetic gas (syngas), producer gas or pyrolysis gas.

52 Claims, No Drawings

PRODUCTION OF FUEL

CROSS-REFERENCE TO RELATED APPLICATION

This application is a 35 USC §371 National Stage application of International Application No. PCT/US2014/042771 filed Jun. 17, 2014, now pending; which claims the benefit under 35 USC §119(e) to U.S. Application Ser. No. 61/838,103 filed Jun. 21, 2013. The disclosure of each of the prior applications is considered part of and is incorporated by reference in the disclosure of this application.

FIELD OF THE INVENTION

The present invention relates generally to fuels and more particularly to methods for processing and producing the same.

BACKGROUND INFORMATION

Dimethyl ether (DME) has recently been identified as a potential fuel of the future. It has several similar properties to propane and liquefied petroleum gas (LPG), and can be used in blends with LPG up to 20% for combustion applications, such as heating and cooking, without modification of the end-use equipment. DME can also be used in blends or by itself in diesel engines after modifications with fuel injectors. In both cases, DME burns cleaner than the traditional fuel, with no particulate or sulfur emissions and very low CO and NOx emissions.

Traditionally, DME is produced from natural gas. Natural gas is reformed through reforming, either auto-thermal reforming or partial oxidation, to generate synthetic gas (syngas). The syngas is cleaned to remove impurities. The syngas is sent to two-step reactor system to convert the syngas to methanol and subsequently to DME. The DME is then purified for the desired grade. The production price of DME from this route will be heavily influenced by the present cost of natural gas. This has been a traditional limitation in the wider use of DME as a fuel product.

More interest in renewable sources has led to generating DME from renewable or inexpensive sources, including coal, coal-bed methane, and stranded natural gas. These streams can also include waste streams such as wood chips, black liquor, municipal solid waste (MSW), refuse-derived waste (RDF), plastics, paper, seed oil, and agricultural waste. When using solid waste feedstock like MSW, the solid material is converted to syngas through pyrolysis and/or gasification. The syngas is then cleaned and converted to DME as with the natural gas process to DME. The production cost using waste streams will be much lower than if using natural gas, and is seen as an advantageous route towards inexpensive DME. The availability of such waste streams may be limited in both amount and composition, and may not be sufficient to meet the increased demand for DME as a fuel.

A key issue with using waste streams, particularly MSW, to produce DME or other liquid fuels is that it will not have consistent composition. MSW has long-term, seasonal, and short-term variations in its composition. This in turn affects the quality of the syngas produced, specifically the ratio of hydrogen to carbon monoxide. For optimal DME production, this ratio is in a range between 1 to 2. DME production technology can tolerate small variation both high and low in those ratios. Wider variances can lead to inefficient and potentially unsafe operation. The variation of hydrogen-to-carbon monoxide ratio generated from MSW may be too large without additional processes and process controls to maintain safe and efficient DME production.

SUMMARY OF THE INVENTION

The present invention relates to fuels and more particularly to methods that combine 2 or more component feedstock streams through processing equipment to generate a common intermediate which may be further converted into a desired product, such as but not limited to a chemical, a fuel, or power, such as electricity. As such, in one aspect, the present invention provides a process for the production of a commodity using two or more feedstock streams. Each feedstock stream is processed into a common intermediate and subsequently processed into a final product, such as electrical energy, a liquid fuel or a liquefied fuel, such as methanol, dimethyl ether, synthetic gasoline, diesel, kerosene, or jet fuel. The common intermediate may be synthetic gas (syngas), producer gas or pyrolysis gas.

DETAILED DESCRIPTION OF THE INVENTION

The present invention relates to fuels and more particularly to methods that combine 2 or more component feedstock streams through processing equipment to generate a common intermediate which may be further converted into a desired product, such as but not limited to a chemical, a fuel, or power, such as electricity.

Before the present methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" or "the process" include one or more methods or processes, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The invention described within is a flexible technology-neutral platform that combines 2 or more component feedstock streams through processing equipment to make a common intermediate to be further converted into a desired product in the form of a chemical, a fuel, or power. The feedstock streams are metered and/or controlled to mitigate chemical and energy content variances in the individual component streams and compensate with one or more component streams to produce a consistent homogeneous (pertaining to its chemical and energy content) intermediate fluid to be further converted into the aforementioned desired product. This platform helps to maintain the chemical and energy content of the intermediate fluid when the economics of one or more of the component feedstock streams are a constraint. The platform allows for a flexible component technology strategy to construct an overall process that will optimize the technical robustness and highest economic value for the desired end product.

One aspect of the platforms technically robust component strategy would be demonstrated in the flexibility of the design choice of using one large processing unit operation (such as pyrolysis/gasification) versus multiple smaller modular units to accomplish the same output capacity. Using the later choice, would achieve a larger apparent turn-down ratio, thus allowing for multiple failures in the discretized modules without negatively impacting the down-steam production capacity and quality of end product. This is due to the ability to use one or more of the other component feedstock streams to make-up for the lost output capacity of the modular units. If the platform required using only one large unit processing operation for a component feedstock stream, and it fails, then the loss the total output component stream would be too great for the other stream(s) to make-up the difference. This platform will provide a higher tolerance for component failure modes and higher reliability of the overall system to produce desired end product.

This platform approach can blend a non-renewable component feedstock with a renewable component feedstock for a desired product, particularly for fuels. This invention can yield a larger amount of a more renewable fuel albeit not 100% renewable. This platform can provide a cleaner desired product that is less hazardous to humans and environment especially in high density or enclosed locations.

An exemplary embodiment of the invention is the production of dimethyl ether (DME) as a fuel. The process involves using a combination of fossil fuels that may or may not be available due to price volatility (such as natural gas, coal, etc . . . ) and a renewable or low-cost feedstock, including but not limited to waste streams such as wood chips, black liquor, municipal solid waste (MSW), refuge-derived waste (RDF), plastics, and paper.

The process includes (at least) two major process flows:
1) One process of converting natural gas to syngas through reforming.
2) One or more processes of converting waste streams to syngas through gasification.

The two effluent streams are combined into a single syngas stream to then convert into DME.

A third stream using anaerobic digestion is available when using wastes with high organic content, like MSW. The MSW would be separated to remove the organic content (such food and agricultural wastes) which possess low energy content and does not gasify well. The sorted MSW (now a RDF) is gasified as described above. The organic content of the MSW is used in anaerobic digesters as to generate methane gas. This methane gas can be reformed in the same manner as the natural gas. There are other possible waste streams beyond the MSW such as agricultural waste that can also be feed directly to this digester to generate methane and offset natural gas. This third stream has the potential to further reduce the required consumption of natural gas and further reduce the production cost of DME.

A fourth possible feedstock stream becomes available when anaerobic digestion is used. The residue of the anaerobic digestion of MSW will be a cake-like substance with up to 70% moisture content. This cake can dewatered to produce a high-energy content waste material that can be processed as additional feed into the waste gasification system along with the RDF. This can be used to offset the amount of MSW required to generate DME, and can help regulate short-term fluctuations in the composition of the MSW, such as seasonal variations.

The primary benefit of this mixture is to reduce the fluctuation in the syngas stream quality that is generated by gasification of MSW and digester residue cake and reforming of anaerobic digester methane. The syngas produced by natural gas reforming will be very consistent compared with the syngas from the other streams. This can be used as a control mechanism to temper the fluctuations and prevent the syngas composition from falling outside the optimal range for DME production. This can apply for other types of wastes, and for other liquid fuels that can be produced from syngas, including but not limited to methanol, ethanol, gasoline, diesel, or jet fuels.

To demonstrate, suppose a MSW gasification steam produces a syngas product that nominally contain a hydrogen-to-carbon monoxide ratio of 2, but can vary from 1.75 to 2.25. The DME process is designed for syngas feedstock with hydrogen-to-carbon monoxide ratio of 2, but can tolerate between 1.9 and 2.1. The MSW-generated syngas would not have sufficient consistency to use within the DME process without consequences. Syngas produced by natural gas can be kept with a consistent hydrogen-to-carbon monoxide ratio of 2. 40 tons/hr of MSW-generated syngas can be mixed to 60 tons/hr of natural-gas derived syngas to maintain 100 tons/hr of net syngas with appropriate consistency for the DME process.

In considering a complete plant that includes syngas generated from MSW and natural gas, the percent of natural gas that comes from MSW can range from 0% to 100%. However, in the embodiment of this technology platform, the percent would likely range from 20 to 50%. Using less than 20% MSW would require a large natural gas reforming plant relative to the MSW gasification side and would have little overall benefit compared to a full natural gas plant. The variances in syngas composition would not be as easy to temper when more than 50% of the syngas is produced by MSW gasification.

There are several secondary benefits of using multiple feedstocks in addition to natural gas to produce DME is to reduce natural gas consumption and lower the net production cost of DME. When natural gas is used as the only feedstock, up to 75% of the DME production price will come from natural gas expenditures. Natural gas prices have both seasonal and long-term fluctuations. The variability of price will significantly impact the economics of a DME plant. By using other feedstocks, such as MSW, the net utility of natural gas is reduced and the production price will remain more stable.

Another advantage of the mixed stream approach is to minimize the impact of fluctuations in the waste feedstocks on the DME production process. Waste feedstocks will have short- and long-term variations in composition. The syngas produced by gasification will change with these variations. Some changes can be tempered by control and operating strategy on gasification, but other factors like a shortage of MSW cannot be resolved solely by changing the gasification parameters. Natural gas and methane feedstock composition will not have significant variations, and the composition of the syngas will be consistent for DME production. The mix of syngases from gasification and from reforming will have an overall stable composition to maintain high DME production rates.

This multiple feedstock platform approach described is not tied to any specific process for natural gas reforming, gasification, gas cleanup, or DME production. For example, there are two-step and one-step DME production processes.

The two-step process is well-established but has some thermodynamic and equilibrium limitations that can reduce syngas conversion. The newer one-step process removes those limitations but it is a technology still in developed. The mixed feedstock approach described here can work with either two- or one-step DME production processes. This multiple feedstock platform approach described above does not require fossil fuels (natural gas, coal, etc . . . ) to be in combination as one of the input streams being processed into power or fuel. All streams can be made from non-fossil fuel feedstock when available for desired fuel-type and process depending. This approach that uses at least one non-fossil fuel in combination with a fossil fuel can yield a larger amount of a more renewable fuel albeit not 100% renewable.

An exemplary embodiment of this invention is to produce DME fuel for mining applications. Mines require diesel fuel to operate prime movers and other equipment (this would pertain to hybrid diesel-electric motors used in mining equipment) for extraction and material handling, approximately 1.06 gals for every ton of ore moved. DME works as a substitute for diesel, requiring some modifications of the diesel equipment to handle DME's lower volumetric energy, and possesses similar or better engine efficiency as diesel. DME is non-toxic and burns cleaner than diesel, with nearly no particular matter or hydrocarbon exhaust. Engine emissions are a high concern for underground mining applications where human health may be at risk from exhaust emissions. DME thus can be used as a better fuel for mining operations; this option becomes more beneficial when considering coal mining, where coal can be used as one of the feedstocks for gasification in the production process to produce DME; this would create a "sustainable" cradle-to-cradle method for these mines to provide their own fuel for operation.

Another preferred embodiment for this patent is for use of fuel production (DME, gasoline, and others) from oil-rich bio-crops like camelina, jatropha, rapeseed, sunflower, and soybean. These plants have been highlighted as their oils can be extracted and upgraded for use as diesel or jet fuel. The solid residue of the plants remain rich in carbon and hydrogen, and thus can be used as a gasification feedstock to make syngas, along with another feedstock like natural gas, coal, MSW/RDF, or other material. The syngas can then go on to make fuel products like DME or gasoline. This is another cradle-to-cradle solution, avoiding the wastes normally associated with the disposal of the otherwise-unused plant remains.

The following examples are provided to further illustrate the embodiments of the present invention, but are not intended to limit the scope of the invention. While they are typical of those that might be used, other procedures, methodologies, or techniques known to those skilled in the art may alternatively be used.

Another embodiment of this patent is to make industrial chemicals that can be derived from DME made from at least one renewable feedstock that are otherwise traditionally derived from the off-products of oil, gas, and coal plants. DME can be made in a number of valuable chemical intermediates, including ethylene, propylene, other alpha olefins, methyl acetate, acetic acid, aromatics, and ethylene glycol. Many of these are used to make polymers and plastics; for example, propylene is used to make both polypropylene polymer which is a common material for fabric, carpets, containers and laboratory equipment, and polyacrylonitrile polymer, a primary component of acrylic materials and the reagent used to make carbon fibers for strengthening composite materials. Propylene is normally produced as a side product from oil and gas refining and would not be considered renewable. The platform technology in this patent can be used with at least one renewable feedstock to produce DME and subsequently into propylene in a more renewable form than from oil and gas refining. The resulting polymer products would thus be considered more renewable than those produced only from propylene from refining processes. Further, these products, at their end-of-life, can be used as solid feedstock for this platform technology, to be broken down and reformed into useful products, creating a cradle-to-cradle lifecycle for the materials.

EXAMPLE I

Production of a Commodity Using Two or More Feedstock Streams

An example of a plant of the present invention is discussed as follows. The net production of the plant is 2000 tpd of DME. This is achieved by using natural gas and MSW. One-half of the DME will be made from syngas generated from MSW. The remaining one-half will be generated from syngas that is produced from the reforming of natural gas and methane.

Approximately 9000 tpd of MSW is available to this plant that is processed into RDF. This produces enough syngas to make 1000 tpd of DME.

The remaining MSW will be primarily organic material and will be sent to an anaerobic digester and/or a dryer that could increase the processed material for input to produce more product. Approximately 760 tpd of methane will be produced from this MSW.

Approximately 900 tpd of natural gas along would be needed to make 1000 tpd of DME. The methane from anaerobic digestion will offset this requirement, and only 140 tpd of natural gas would be required.

A full 2000 tpd DME plant using only MSW feedstock could be built, and could require up to 18000 tpd of MSW to be available. This quantity of MSW is on the order of the waste production from a large metropolitan city and will not be likely available in all areas where DME would be used. The multiple feedstock approach balances the consumption of natural gas and the reasonable availability of MSW.

A financial analysis was performed across four specific scenarios for producing 2000 tpd DME.

1) Using only natural gas to make DME
2) Using only MSW to make DME
3) Using a mix of natural gas and MSW to make DME but without any anaerobic digestion.
4) Using a mix of natural gas and MSW to make DME with anaerobic digestion.

Capital, production, and operation costs were estimated from vendor prices and current costs (as of May 2013) for a 2000 tpd DME plant with a 20 year lifetime.

The production cost of DME from each of these scenarios is shown in the table below, based on a delivered natural gas price of $6/MMBTU. The production cost is calculated as the sum of the total capital cost and the total operating costs over the 20 year lifetime, divided by the total production of DME over the plant lifetime.

|  | Natural Gas Only | MSW Only | Natural Gas + MSW (no digester gas) | Natural Gas + MSW and Digester Gas |
|---|---|---|---|---|
| Production Price ($/ton DME) | $365.21 | $263.79 | $324.25 | $216.20 |

As shown, using MSW and digester gas will offset the consumption of natural gas even with the added costs of gasification and digester equipment. The example embodiment using natural gas, MSW, and digester gas, is lower than the natural gas-only case by $149/ton DME, about a 40% reduction.

These values are calculated at a natural gas delivery price at $6/MMBTU. The effect of the variability of natural gas costs on the production costs is shown in the table below using a range of natural gas costs from $6 to $14/MMBTU.

| Natural Gas Cost | Natural Gas Only | MSW Only | Natural Gas + MSW (no digester gas) | Natural Gas + MSW and Digester Gas |
|---|---|---|---|---|
| $6/MMBTU | $365.21 | $263.79 | $324.25 | $216.20 |
| $8/MMBTU | $454.10 | $263.79 | $368.70 | $222.51 |
| $10/MMBTU | $540.40 | $263.79 | $411.85 | $228.64 |
| $12/MMBTU | $626.70 | $263.79 | $455.00 | $234.76 |
| $14/MMBTU | $713.00 | $263.79 | $498.15 | $240.89 |

Using MSW with or without digester gas helps to reduce the impact of the natural gas price on the production price of DME compared to the first case where only natural gas is used. Using digester gas further stabilizes the production price for DME. There is no change in the production price in using MSW only, but as previously stated, obtaining the waste for a plant at this scale would be expected to be difficult. Therefore, the scenario using a combination of natural gas, MSW, and digester gas balances the desire to stabilize production costs against rising natural gas prices while offering a reasonable scale for MSW utilization.

Another benefit of this approach involves modular units and maintenance of the total plant output when one or more modules become unavailable. Modular units are used to provide redundancy for certain feedstock processing units to overcome longer downtime that these units may undergo. Using multiple feedstock processing streams allows the overall plant to mitigate these downtimes by shifting production of the common intermediate to the other feedstock processing, within their safety and tolerance limits, so that the target production continues at scale.

The exemplary embodiment using the mix of MSW and natural gas demonstrates this benefit. A single natural gas-to-syngas process can be built at a range of scales. Gasification units can be built in modules from 25 to 500 tons of feedstock per day, with units in the 75-350 tons per day being optimal for highest energy conversion while balancing economic factors. Gasification units are prone to frequent maintenance periods and downtimes compared to the natural gas plant. The gasification system described for the 2000 tons per day DME plant would require approximately 9000 tons per day of MSW feedstock, requiring a number of gasification modules. The optimal design of this plant would be based on balancing the operating range of the natural gas plant with the module size and availability of the gasification plant such that the plant would continue to produce 2000 tons per day DME even if one or more of the gasification modules are offline. The use of gasification modules would help to mitigate issues that would arise from the variable quality of the MSW, as well as any temporary loss of supply of MSW.

Continuing from above preferred embodiment, this example plant would be sized so that the natural gas plant is providing ½ of the syngas to make DME (1000 tpd DME) while the modular gasification system would provide syngas to make up the remaining 1000 tpd DME from 9000 MSW. The natural gas plant has an estimated 20% off-design point range in which it can operate safely. That is, with more natural gas feedstock, the natural gas plant can safely operate to produce 20% more syngas equivalent to 200 tpd of DME, or a net 1200 tpd of DME. In turn, the overall DME plant will not lose its 2000 tpd DME production rate as long as the gasification process can continue to continuously produce syngas equivalent to 800 tpd DME. This would require the gasification modules to process a minimum of 7200 tpd of MSW at all times. Here, smaller modules in the range of 225-450 tpd MSW would be preferable. If the gasification system was composed of 15 modules at 600 tpd MSW each, then two or three of these modules (20%) could be offline at any time and still have the overall plant be able to produce 2000 tpd of DME. On the other hand, using ten modules at 900 tpd MSW each, only one module could be down at any time (11%); if two modules are offline, the production of DME will be affected. The optimum gasification module will be a function of the technical aspects of the respective technologies, and the financial analysis of the process, including the losses associated with failing to meet the production goals for the plant One embodiment of this patent is to build a process that produces fuel, such as diesel, gasoline, or DME, that can be used in the development of one of the feedstocks that is used in the process, creating a type of sustainable process. Such cycles can be ideal in remote locations where obtaining fuel or feedstock could be difficult, and would allow such sites to create their own fuel for their needs. Such an approach can be of a significant economic benefit as well as improve the net energy efficiency of the target location.

A more detailed embodiment of this patent in regards to the sustainable nature process described above is for mining applications, where one of the feedstocks is coal that is mined. A portion of the coal can be gasified to syngas. This syngas can be mixed with other syngas produced from natural gas, MSW/RDF, biomass, agricultural waste or other available feedstock to make DME, which in turn can be used to power the prime movers and other equipment for the mine.

Another embodiment of this patent that demonstrates the sustainable concept is to produce a fuel product that is used as part of a biomass cultivation cycle. The cultivation and harvesting of these crops will require fuel like diesel or gasoline for the farming equipment. DME as previously described can be a replacement for diesel systems with the same or better conversion efficiency, while gasoline can be produced from syngas by first producing methanol. These biomass systems are expected to generate enough fuel for the harvesting requirements.

Although the invention has been described with reference to the above example, it will be understood that modifications and variations are encompassed within the spirit and scope of the invention. Accordingly, the invention is limited only by the following claims.

What is claimed is:

1. A process for the production of a commodity using two or more feedstock streams,
   wherein each feedstock stream is processed into a common intermediate and subsequently processed into a final product, thereby producing the commodity,
   wherein each feedstock stream is selected from the group consisting of methane, natural gas, liquefied petroleum gas, coal, coal-bed methane, biomass, natural resources, waste products, and renewable materials,
   wherein the common intermediate is one or more of the components selected from the group consisting of hydrogen, carbon monoxide, synthetic gas (syngas), producer gas, and pyrolysis gas,
   wherein the final product or commodity is one or more of the components selected from the group consisting of electrical energy, liquid fuel, liquefied fuel, methanol, and dimethyl ether (DME),
   wherein at least one of the two or more feedstock streams has a reduced temporal average composition variance as compared to a second of the two or more feedstock streams, and
   wherein the reduced variance is at most 25% of the variance of the second feedstock stream.

2. The process of claim 1, wherein the final product or commodity is electrical energy.

3. The process of claim 1, wherein the final product or commodity is a liquid fuel or a liquefied fuel.

4. The process of claim 3, wherein the final product or commodity is methanol.

5. The process of claim 3, wherein the final product or commodity is dimethyl ether.

6. The process of claim 3, wherein the final product or commodity is synthetic gasoline, diesel, kerosene, or jet fuel.

7. The process of claim 1, wherein the common intermediate is synthetic gas (syngas).

8. The process of claim 1, wherein the common intermediate is producer gas or pyrolysis gas.

9. The process of claim 1, wherein throughput ratio of the reduced variance feedstock stream to the second feedstock stream is adjusted to reduce the variance of the common intermediate.

10. The process of claim 1, wherein at least one of the two or more feedstock streams is natural gas.

11. The process of claim 1, wherein at least one of the two or more feedstock streams is liquefied petroleum gas.

12. The process of claim 1, wherein at least one of the two or more feedstock streams is biomass.

13. The process of claim 12, wherein the feedstock stream is cellulosic biomass selected from the group consisting of woodchips, wheat straw, and switchgrass.

14. The process of claim 12, wherein the feedstock stream is an energy crop.

15. The process of claim 12, wherein the feedstock stream is a residual organic cake product from oil extraction from oil-seed plants selected from the group consisting of camelina and jatropha.

16. The process of claim 1, wherein at least one of the two or more feedstock streams is a waste product.

17. The process of claim 16, wherein the feedstock stream is selected from the group consisting of municipal solid waste, refuse-derived fuel, sewage sludge, food waste, agricultural waste, paper, cardboard, and plastic.

18. The process of claim 16, wherein the feedstock stream is an industrial waste product selected from the group consisting of sawdust, paper pulp, and petroleum coke (pet coke).

19. The process of claim 16, wherein the feedstock stream is a methane-rich gas obtained from a landfill, agricultural waste, or a waste digestion system.

20. The process of claim 1, wherein at least one of the two or more feedstock streams is a natural resource.

21. The process of claim 20, wherein the feedstock stream is coal.

22. The process of claim 20, wherein the feedstock stream is coal-bed methane.

23. The process of claim 20, wherein the feedstock stream is obtained from stranded gas reserves.

24. The process of claim 1, wherein conversion of at least one of the two or more feedstock streams to the common intermediate is via thermochemical conversion.

25. The process of claim 24, wherein conversion of at least one of the two or more feedstock streams is through torrefaction.

26. The process of claim 24, wherein the conversion of at least one of the two or more feedstock streams is through aerobic or anaerobic pyrolysis.

27. The process of claim 24, wherein the conversion of at least one of the two or more feedstock streams is through air or steam-based gasification.

28. The process of claim 24, wherein the conversion of at least one of the two or more feedstock stream is through reformation selected from the group consisting of steam reforming, partial oxidation, and auto-thermal reforming.

29. The process of claim 1, wherein the conversion of each feedstock stream to the common intermediate occurs in a processing unit.

30. The process of claim 1, wherein the conversion of the two or more feedstock streams to the common intermediate occurs in a combined processing unit.

31. The process of claim 1, wherein at least one of the two or more feedstock streams, prior to the processing of the common intermediate to the final product or commodity, are treated by the same processing units to clean up and purify the final product or commodity.

32. The process of claim 1, wherein feedstock stream processing and final product processing are performed in units having a modular design.

33. The process of claim 32, wherein sizing of the feedstock stream and final product processing stages, and size of their modular design, is determined at a level that maximizes the continuous production of the desired product at the target output levels.

34. The process of claim 1, wherein the final product or commodity is used as an energy source for the equipment used to gather or bring one or more of the feedstock streams to the process.

35. The process of claim 1, wherein the primary application of the process is related to mining.

36. The process of claim 35, wherein the final product or commodity is DME fuel suitable for use as a replacement for diesel-based prime movers and other machinery used in mining applications wherein the reduction of combustion by-product contaminants is desired and/or regulated.

37. The process of claim 36, wherein the final product is DME fuel suitable for use as a replacement for carbonaceous soot, carbon monoxide, sulfur, nitrogen oxide, or unreacted hydrocarbons.

38. The process of claim 36, wherein the primary application is coal mining, and wherein the coal is used within gasification processes to make DME for mining prime movers and other machinery.

39. The process of claim 35, wherein the final product or commodity is DME or gasoline fuel suitable for harvesting and transformation of oilseed biocrops.

40. The process of claim 39, wherein the oilseed biocrop is selected from the group consisting of camelina, jatropha, sunflower, soybeans, and rapeseed.

41. The process of claim 40, wherein the oilseed biocrop application comprises the use of the post-extracted plant remains to produce DME or gasoline by this process for fuel for planting and harvesting equipment.

42. The process of claim 1, wherein at least one of the two or more feedstock streams is a renewable material, and the final product or commodity from the process is dimethyl ether.

43. The process of claim 42, wherein the dimethyl ether is used to produce industrial chemicals, reagents and solvents, selected from the group consisting of ethylene, propylene, other alpha olefins, methyl acetate, acetic acid, benzene, toluene, xylene, and ethylene glycol.

44. The process of claim 43 wherein the industrial chemicals, reagents, and solvents are used to produce polymers and subsequent derivatives selected from the group consisting of polyethylene, polyvinyl chlorides, polypropylene, polyacrylonitrile, carbon fibers, polyester, polyvinyl acetate, co-polymers, and strengthening agents for polymers.

45. A process for the production of a commodity using two or more feedstock streams, wherein each feedstock stream is processed into a common intermediate and subsequently processed into a final product, thereby producing the commodity, wherein the process further comprises using the final product or commodity as an energy source for the equipment used to gather or bring one or more of the feedstock streams to the process,
   wherein each feedstock stream is selected from the group consisting of methane, natural gas, liquefied petroleum gas, coal, coal-bed methane, biomass, natural resources, waste products, and renewable materials,
   wherein the common intermediate is one or more of the components selected from the group consisting of hydrogen, carbon monoxide, synthetic gas (syngas), producer gas, and pyrolysis gas,
   wherein the final product or commodity is one or more of the components selected from the group consisting of electrical energy, liquid fuel, liquefied fuel, methanol, and dimethyl ether (DME),
   wherein at least one of the two or more feedstock streams has a reduced temporal average composition variance as compared to a second of the two or more feedstock streams, and
   wherein the reduced variance is at most 25% of the variance of the second feedstock stream.

46. A process for the production of a commodity using two or more feedstock streams, wherein each feedstock stream is processed into a common intermediate and subsequently processed into a final product, thereby producing the commodity, wherein the process further comprises applying the process to mining applications,
   wherein each feedstock stream is selected from the group consisting of methane, natural gas, liquefied petroleum gas, coal, coal-bed methane, biomass, natural resources, waste products, and renewable materials,
   wherein the common intermediate is one or more of the components selected from the group consisting of hydrogen, carbon monoxide, synthetic gas (syngas), producer gas, and pyrolysis gas,
   wherein the final product or commodity is one or more of the components selected from the group consisting of electrical energy, liquid fuel, liquefied fuel, methanol, and dimethyl ether (DME),
   wherein at least one of the two or more feedstock streams has a reduced temporal average composition variance as compared to a second of the two or more feedstock streams, and
   wherein the reduced variance is at most 25% of the variance of the second feedstock stream.

47. The process of claim 46, wherein the final product or commodity is DME fuel suitable for use as a replacement for diesel-based prime movers and other machinery used in mining applications where the reduction of combustion by-product contaminants is desired and/or regulated.

48. The process of claim 47, wherein the final product or commodity is DME fuel suitable for use as a replacement for carbonaceous soot, carbon monoxide, sulfur, nitrogen oxide, or unreacted hydrocarbons.

49. The process of claim 47, wherein the primary application is coal mining, and wherein the coal is used within gasification processes to make DME for mining prime movers and other machinery.

50. The process of claim 46, wherein the product is DME or gasoline fuel suitable for harvesting and transformation of oilseed biocrops.

51. The process of claim 50, wherein the oilseed biocrop is selected from the group consisting of camelina, jatropha, sunflower, soybeans, and rapeseed.

52. The process of claim 51, wherein the oilseed biocrop application comprises the use of the post-extracted plant remains to produce DME or gasoline by this process for fuel for planting and harvesting equipment.

* * * * *